United States Patent [19]

Uldall

[11] Patent Number: 4,493,696
[45] Date of Patent: Jan. 15, 1985

[54] HEMODIALYSIS CANNULAR FOR SUBCLAVIAN INSERTION

[75] Inventor: Peter R. Uldall, Willowdale, Canada

[73] Assignee: Allentyne Limited, Willowdale, Canada

[21] Appl. No.: 608,257

[22] Filed: May 4, 1984

Related U.S. Application Data

[63] Continuation of Ser. No. 160,316, Jun. 17, 1980, abandoned.

[30] Foreign Application Priority Data

Dec. 28, 1979 [CA] Canada .................................. 342787

[51] Int. Cl.³ .............................................. A61M 5/00
[52] U.S. Cl. ...................................... 604/43; 604/164
[58] Field of Search ................................. 604/43–45, 604/53, 27, 28, 158, 161, 264, 280

[56] References Cited

U.S. PATENT DOCUMENTS

| | | | |
|---|---|---|---|
| 4,016,506 | 4/1977 | Koehn | 331/96 |
| 4,037,599 | 7/1977 | Raulerson | 604/44 |
| 4,129,129 | 12/1978 | Amrine | 128/214 |
| 4,492,384 | 1/1985 | Kaslow | 277/237 |

FOREIGN PATENT DOCUMENTS

| | | |
|---|---|---|
| 0000041 | 12/1978 | European Pat. Off. . |
| 3006291 | 8/1980 | Fed. Rep. of Germany . |
| 1284537 | 8/1978 | United Kingdom . |
| 2017499 | 10/1979 | United Kingdom . |
| 2044107 | 10/1980 | United Kingdom . |

Primary Examiner—Stephen C. Pellegrino
Attorney, Agent, or Firm—Ridout & Maybee

[57] ABSTRACT

A double lumen cannula for hemodialysis and similar applications such as haemoperfusion comprises elongated flexible tubular members, disposed one within the other, for semi-permanent insertion into the sub-clavian vein of a patient, leaving semi-permanent access thereto for repeated hemodialysis treatments. The cannula is formed of an elongated flexible outer member, having a smooth exterior surface, and made up of an elongated main portion, a convergent, constricting portion and a narrower distal end portion which is tapered at the tip to fit over a Seldinger guide wire. There is also an inner member having a diameter substantially the same as that of the distal end portion. The inner member is insertable into the outer member to come into sealable engagement with the interior walls of the constricting portion, so as to form a continuous inner lumen with the distal end portion of the outer member, and is removable therefrom for removal of clot or replacement purposes. Both members are sufficiently flexible to permit curving thereof on a 12 cm radius without reduction in internal cross section thereof, i.e. without substantial kinking or buckling, so as to avoid constriction of fluid flows. Because the cannula provides two pathways for simultaneous extraction and return of blood there is no need to use a single needle machine to produce an alternating blood flow.

9 Claims, 6 Drawing Figures

HEMODIALYSIS CANNULAR FOR SUBCLAVIAN INSERTION

This application is a continuation of Ser. No. 160,316, filed June 17, 1980, now abandoned.

FIELD OF THE INVENTION

This invention relates to a hemodialysis cannula, and more particularly to a novel form of hemodialysis cannula which can be inserted in semi-permanent manner into the subclavian vein of the patient.

For regular hemodialysis, permanent vascular access is normally provided by means of a surgically constructed arterio-venous fistula, created if possible in advance of need.

The conventional method of conducting hemodialysis on a patient is to introduce into an arterialised vein, normally a lower arm vein, one or two blood flow needles, to remove blood from the patient to the exterior hemodialysis machine and to return the treated blood to the patient at substantially the same location. At least one puncture of the vein needs to be made for such catheter insertion every time the patient undergoes a hemodialysis treatment. Whilst in common practice two separate needle devices are used, one for blood outflow and the other for blood return, there are several proposals for the use of a single catheter provided with co-axially arranged lumen, so as to reduce to one the number of vein punctures required in each hemodialysis treatment. Examples of co-axially arranged metal catheters for use in conventional hemodialysis, in a limb of the patient, are to be found in U.S. Pat. No. 4,037,599 Raulerson; U.S. Pat. No. 4,073,297 Kopp; U.S. Pat. No. 4,134,402 Mahurkar; and U.S. Pat. No. 4,096,860 McLaughlin. All of these examples of prior art show a rigid, metal needle-type catheter for temporary use during the actual hemodialysis or transfusion etc. operation on the patient, and removal once the operation is completed. In each case the rigid inner tube protrudes beyond the outer tube. None is flexible or suitable for insertion into the subclavian vein.

Although the arterio-venous fistula is the standard and accepted method for permanent vascular access, unfortunately, some patients experience end stage renal failure without warning, and established fistulae may fail unexpectedly. With the growth of large programs for long-term peritoneal dialysis, an increasing number of patients require to be transferred at short notice to hemodialysis because of peritonitis. Such patients do not usually have arterio-venous fistulae constructed in advance, since many of them will never need them. Patients on long-term peritoneal dialysis may also need short-term hemodialysis while they undergo abdominal surgery. Transplant recipients whose arterio-venous fistulae have thrombosed may develop acute renal failure. For all these categories of patients, the silastic teflon shunt, though immediately usable, wastes blood vessels and may not be feasible in patients whose access sites have already been used. Temporary peritoneal dialysis is not always a suitable alternative.

There is thus a need for a simple, immediately usable vascular access method which does not destroy blood vessels, and does not limit the patient's mobility. Temporary vascular access for hemodialysis can be obtained with a femoral cannula introduced by the Seldinger technique, normally inserted in the femoral vein. With such prior art device, the patient must be prepared and the catheter applied carefully, by medically trained personnel, prior to every hemodialysis use. For patients with absence of renal function, this can be several times per week. The preparation and application is time-consuming and difficult to perform on an emergency basis. The cannula cannot be left in situ after dialysis if the patient is to remain mobile. Moreover, repeated insertions lead to the build-up of scar tissue at the access sites of the patient. Some means of readily usable, semi-permanent vascular access would be preferable.

SUMMARY OF THE INVENTION

In the present invention, there is provided an indwelling subclavian cannula which is particularly suitable for temporary hemodialysis. When not in use, it remains in situ without restricting the mobility or activities of the patient to any significant extent. The invention provides a double lumen cannula, with the lumens located co-axially, so that only one insertion into the vein of the patient is required. Both of the lumens are elongated and flexible so as to assume the disposition of the subclavian vein. The inner lumen is removable from within the outer lumen, without removing the cannula as a whole from the subclavian vein of the patient, thereby providing for replacement of the inner lumen and cleaning and access of the apparatus as a whole.

Thus according to the present invention, there is provided a double lumen cannula suitable for insertion into a large vein such as the subclavian vein of the patient for blood removal therefrom and blood return thereto, said cannula comprising:

an elongated flexible tubular outer member having a smooth outer surface and comprising a main elongated portion of first cross section, an integral convergent section and an integral distal end portion having a second cross section which is smaller than said first cross section;

a plurality of blood flow apertures, spaced apart from one another, in the side wall of said main portion adjacent the convergent section;

at least one blood flow aperture in said distal end portion;

an elongated flexible tubular inner member having a cross section smaller than said first cross section, the inner member being disposed within the outer member, the distal end of said inner member being disposed in substantially sealing end contact with the convergent section of the outer member so as to form, with the outer member, a pair of concentrically arranged discrete fluid flow lumens, the inner lumen constituted by the said inner member and said distal end portion of the outer member, the outer lumen constituted by the main portion and the convergent section of the outer member;

the inner member being releasable and withdrawable from within the outer member.

The provision of two blood pathways for simultaneous extraction of blood from and return of blood to the patient obviates the need for use of a single needle machine to provide an alternating blood flow.

BRIEF REFERENCE TO THE DRAWINGS

DESCRIPTION OF THE PREFERRED EMBODIMENTS

Figure 1:
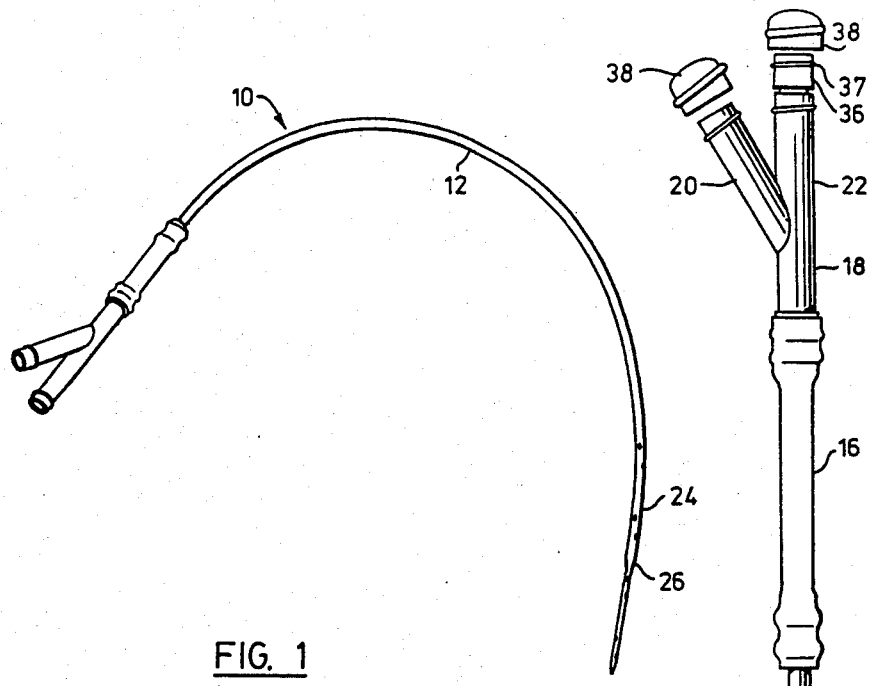
FIG. 1 is a perspective view of a specific preferred embodiment of the present invention.

The cannula according to the present invention is preferable constructed of flexible, radio-opaque tetrafluoroethylene polymer, having known biocompatibility for residence in the patient's body over extended periods of time, having smooth outer surfaces, and having the necessary degree of flexibility to assume the configuration of the subclavian vein and superior vena cava without kinking or buckling or otherwise constricting the flow of fluid therethrough. The length of the outer member should be such that, after proper insertion, the tip lies at the junction of the superior vena cava and right atrium of the patient, whilst extending along the subclavian vein to the exterior of the patient's body. It should not extend past the right atrium, or there is a risk that it may enter the heart. The diameter of the cannula must be small enough so that it does not damage the vein, and should be substantially smaller than the size of the subclavian vein itself. It should nevertheless be large enough to provide two pathways, to give a flow through each pathway of approximately 200 mls per minute, of blood. It must not, of course, have any external projections or the like which might tear the vein.

In addition, the preferred embodiment of the invention has a tapered tip at its distal, to facilitate its insertion, e.g. by the Seldinger technique.

The provision of an inner lumen which is removable from the outer lumen is a significant feature in the device of the present invention. In this arrangement, the inner lumen can be removed from the outer lumen to facilitate initial introduction of the cannula into the subclavian vein. The cannula is best inserted by means of the known Seldinger technique, in which the vein is punctured with a Seldinger needle, having a cuff, and then the needle is removed, leaving the cuff in place. The guidewire is inserted into the vein, through the cuff, the cuff then being removed. Subsequently, the cannula according to the present invention can be inserted over the guidewire, and can at this time contain an obturator, of stiffer but flexible material, so as to ensure that the outer lumen does not buckle or kink during insertion. Once it is safely in place, the obturator can be removed, and the inner lumen can then be inserted. The desirable use of an obturator in this manner is made possible by the feature of removability of the inner lumen.

Moreover, in the situation where the cannula is left inserted in the subclavian vein for two to three weeks, and the cannula is used 3 times per week or more for hemodialysis, it is necessary to ensure than the cannula does not become blocked with blood clots. This is normally done by means of heparin. With the arrangement of the present invention, the inner lumen can be removed, for more thorough cleaning and clot removal from both the inner lumen and the outer lumen. If desired, a specific declotting catheter can be inserted into the outer lumen, once the inner lumen has been removed therefrom.

Moreover, if the inner lumen breaks or cracks, due to its being thinner and weaker than the outer lumen, it can easily be replaced, even while dialysis is being conducted, and does not necessitate the removal and reinsertion of an entire cannula, into the patient. A supply of spare inner lumens can be provided, along with each cannula according to the invention, to safeguard against such emergencies.

The end of the cannula remote from its distal end is normally provided with a medical grade silicone rubber extension, to the end of which is sealingly secured a junction piece. The inner lumen passes through the silicone rubber extension and out through one arm of the junction pieces whilst the other arm of the junction piece is connected to the outer lumen. Then, the junction pieces can be connected to the respective dialysis machine connections. The junction piece suitably has a straight arm, through which the inner lumen passes and a second arm extending at an oblique angle in communication with the outer lumen. It is preferred to adjust the length of the outer lumen so that, when properly inserted, the end of the silastic extension is flush with the patient's skin, and extends outwardly therefrom. The silastic extension provides a means for closing the cannula by applying a clamp thereto. When not in use, the junction ends are suitably closed by means of injection caps with Luer locks. The cannula can be anchored in place by means of a sterile adhesive transparent dressing. One dressing is placed below and under the silastic extension and reflected back, adhesive side up. The second is placed above and overlapping the first, so that the silastic extension is enclosed between two layers of sterile dressing. Thus it is not necessary to suture the cannula in place, and the entry site is protected from contamination. After routine chest X-rays to check the cannula position, it is possible to start hemodialysis immediately. At the conclusion of the procedure, the cannula is flushed with heparinized saline, and both the junction pieces are sealed with injection caps with Luer locks. This allows injection of heparin periodically to maintain patency within both lumens of the cannula. Patients can safely leave the medical treatment facility with the cannula it situ, and the patient can inject the heparin himself when required. It is preferred to maintain the silastic segment closed by a sliding or spring clamp, as a further protection against blood loss or air embolus resulting from a disconnected cap, at all times when the subclavian cannula is not in use for dialysis or heparin injection.

For the average sized, adult patient, the outer member of the cannula should have a length of from about 18 to about 22 cms, for ensuring proper insertion. The combined length of the convergent section and distal end portion is suitable 3–4 cm.

It is also preferred to make both the inner and outer members of the cannula of the invention from a radio-opaque material. Then if necessary the correct installation and positioning of the cannula can be checked periodically.

DETAILED DESCRIPTION OF THE SPECIFIC PREFERRED EMBODIMENT

Referring now to the drawings, a cannula 10 according to the present invention includes a tubular outer member or lumen 12, an insertable and withdrawable inner tubular member or lumen 14, a silicone rubber extension 16 sealingly attached to one end of the outer lumen 12 and a junction piece 18 having two arms 20, 22, the body of the junction piece 18 being attached to the other end of the silicone rubber extension 16, in sealing engagement therewith.

The outer lumen 12 has a main tubular elongated portion 24, an integral convergent section 26 and an integral distal end portion 28 adjoining the convergent section 26. The distal end portion is provided with a tapered end 29, an end aperture 30 and a series of spirally arranged, separate side apertures 32. The main portion 24 is also provided with a series of separate, spirally arranged side apertures 34.

The inner lumen 14 has a cross sectional outer diameter substantially the same as that of the inner diameter of the distal end portion 28 of outer member 12, and is small enough to leave clearance between the side wall of outer member 12 and the side wall of inner member 14, over the length of the main portion 24 of outer lumen 12. The inner member 14 projects outwardly through arm 22 of junction piece 18, which is arranged in a straight relationship with the silastic extension 16. The inner member 14 has an enlarged end extremity 36, a male Luer lock thread 37 at its end, to receive a female Luer lock injection cap 38. End extremity 36 projects outwardly through the end of arm 22 when the inner member 14 is properly in position.

Figure 3:
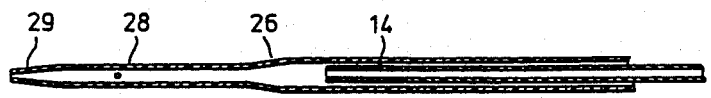
FIG. 3 is a cross section in detail of the end of the cannula, with the inner lumen withdrawn.
Figure 4:
FIG. 4 is a view similar to FIG. 3, but with the inner lumen in sealing engagement and contact with the outer lumen.
Figure 2:
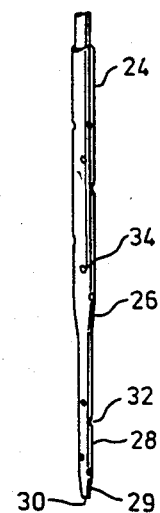
FIG. 2 is a view similar to FIG. 1, on a larger scale, and omitting the middle part of cannula.
Figure 5:
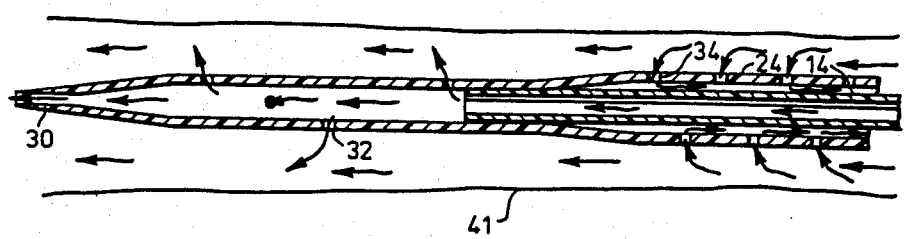
FIG. 5 is a diagramatic cross sectional view similar to FIG. 4 showing in schematic representation the path taken by blood during hemodialysis with the cannula in place.

As shown in FIGS. 3 and 4, the inner member 14 is withdrawable from within the outer member 12, and can in fact be withdrawn all the way through extension 16 and junction piece 18. When it is inserted into the outer member 12, as shown in FIG. 4, it is pushed forwardly through outer member 12 until its end comes into engagement with convergent section 26 of outer member 12. At this position, the inner member 14 seals against the inner walls of outer member 12, and the inner member forms, with the distal end portion 28 of the outer member, a continuous inner lumen isolated from and fluid tight sealed from the outer lumen formed between the inner wall of outer member 12 and the outer wall of inner member 14. End aperture 30 and side apertures 32 in distal end portion 28 now constitute apertures for the inner lumen of the cannula. Side apertures 34 of the main portion of the outer member 12 now form apertures in the outer lumen of the cannula. When conducting a hemodialysis operation using the cannula of the present invention, blood return flow to the subclavian vein is through the inner lumen 14 and apertures 30, 32, and simultaneously blood withdrawal from the vein for dialysis treatment is through apertures 26 and outer lumen 12, and hence through arm 20 of the junction piece 18 to the machine. As shown in FIG. 5, the outer and inner lumens constitute separate, clear blood flow passageways when assembled together. The direction of blood flow, with the cannula disposed within a vein 41 is as indicated on FIG. 5. In this arrangement, treated blood is returned downstream in the vein from the location of blood withdrawal, so as to exclude the possibility of mixing within the vein of treated and untreated blood.

Figure 6:
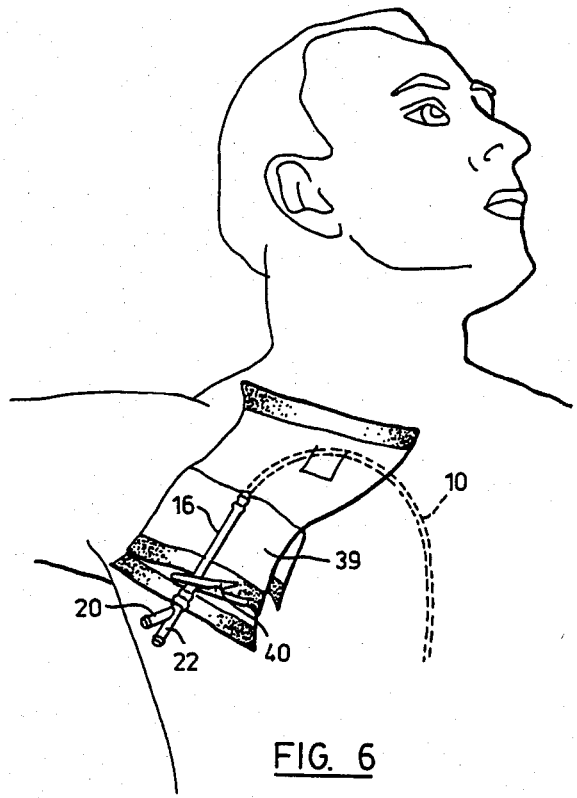
FIG. 6 is a diagramatic view showing the cannula of the present invention in place in the subclavian vein of a patient.

FIG. 6 shows the subclavian hemodialysis cannula of the present invention in position on the patient, when not in use for dialysis. The cannula is secured in position by means of adhesive dressings 39, with the rubber extension thereof 16 protruding through the dressings. A clamp 40 closes the rubber extension, when not in use, so as to guard against air ingress or contamination in the event that the junction arms 20, 22 become accidentally opened.

The use of a subclavian cannula as described herein largely solves the problem of temporary vascular access. Hemodialysis can be started within 20 minutes, even if the patient has no definitive permanent access. Moreover, this is done without jeopardizing future sites for arterio-venous fistula construction. Hemodialysis does not have to be delayed or postponed. Because shunts are not inserted, patients do not have to stay in hospital while shunt sites heal. Blood vessels are not destroyed, and unsightly scars are avoided. A subclavian cannula according to the invention can be inserted and the patient can go home on the same day. The cannula is well tolerated by patients both in hospital and at home. It does not significantly restrict mobility or activities. It causes no more than minimal discomfort during insertion. After it has been removed, the subclavicular scars are inconspicuous.

Whilst a specific preferred embodiment of the present invention has been illustrated and described herein in detail, it will be appreciated that this is by way of example only, and is not to be construed to be limiting. The scope of the present invention is limited only by the scope of the appended claims.

For example the same principle can be applied when dialysis or haemoperfusion for poisoning is conducted through the femoral vein. A longer cannula of the same basic design can be introduced into the inferior vena cava via the femoral vein. This will avoid the necessity of inserting two single lumen femoral cannulae.

What is claimed is:

1. A double lumen cannula suitable for insertion into a large vein such as the subclavian vein of a patient for blood removal therefrom and blood return thereto, said cannula comprising an elongated flexible tubular outer member comprising a main elongated portion of first cross section, an integral convergent section having a smooth continuous outer surface and a flexible distal end portion having a second cross section which is smaller than said first cross section a plurality of blood flow apertures, spaced apart from one another in the side wall of said main portion of said first cross section adjacent the convergent section;

at least one blood flow aperture disposed centrally in the tip of said flexible distal end portion;

an elongated flexible tubular inner member having an opening at each end and having a cross section smaller than said first cross section, the inner member being disposed within the outer member, the distal end of said inner member being disposed in substantially sealing end contact with the convergent section of the outer member so as to form, with the outer member, a pair of concentrically arranged discrete fluid flow lumens, the inner lumen constituted by said inner member and said distal end portion of the outer member, the outer lumen constituted by the main portion and the convergent section of the outer member;

the inner member being releasable and withdrawable from within the outer member.

2. The cannula of claim 1 wherein said distal end portion of the outer member has a plurality of blood flow apertures, one said aperture being axially presented at the end thereof, the other said apertures being spaced apart from one another in the side wall thereof.

3. The cannula of claim 2 including a junction piece on the end of said main portion, the inner member passing through one branch of said junction piece.

4. The cannula of claim 3 wherein the outer member has a length from about 18–22 cm, from its distal end portion extremity to its junction piece connection.

5. The cannula of claim 4 wherein the combined length of convergent section and the distal end portion of said outer member is from about 3 to about 4 cm.

6. The cannula of claim 5 wherein the blood flow aperture in the side wall of the main portion of the outer member are arranged in a spiral formation.

7. The cannula of claim 6 wherein the blood flow apertures in the side wall of distal end portion of the outer member are arranged in a spiral formation.

8. The cannula of claim 3 having connected between the outer member and the junction piece a tubular elastic extension which can be sealed with a clamp.

9. The cannula of claim 1 in which the end of the outer member remote from the distal end portion connects to a tubular elastic extension which can be sealed with a clamp.

* * * * *